US008895282B2

(12) United States Patent
Tano

(10) Patent No.: US 8,895,282 B2
(45) Date of Patent: Nov. 25, 2014

(54) USE OF A SUBSTANCE FOR MANUFACTURING OF A MEDICAMENT FOR TREATMENT OF COMMON COLD

(75) Inventor: Krister Tano, Boden (SE)

(73) Assignee: Tanomed AB, Umea (SE)

( * ) Notice: Subject to any disclaimer, the term of this patent is extended or adjusted under 35 U.S.C. 154(b) by 737 days.

(21) Appl. No.: 12/933,438

(22) PCT Filed: Mar. 20, 2009

(86) PCT No.: PCT/SE2009/050291
§ 371 (c)(1),
(2), (4) Date: Nov. 3, 2010

(87) PCT Pub. No.: WO2009/116944
PCT Pub. Date: Sep. 24, 2009

(65) Prior Publication Data
US 2011/0044966 A1 Feb. 24, 2011

(30) Foreign Application Priority Data

Mar. 20, 2008 (SE) ...................................... 0800658

(51) Int. Cl.
A61K 38/44 (2006.01)
A61K 38/43 (2006.01)
C12N 9/04 (2006.01)
A61K 38/47 (2006.01)
A61K 45/06 (2006.01)
A61K 38/00 (2006.01)
C07K 14/095 (2006.01)
A61K 33/40 (2006.01)

(52) U.S. Cl.
CPC ............... A61K 33/40 (2013.01); A61K 38/443 (2013.01); A61K 38/47 (2013.01); A61K 45/06 (2013.01)
USPC .......... 435/190; 424/616; 424/94.1; 424/94.2

(58) Field of Classification Search
None
See application file for complete search history.

(56) References Cited

U.S. PATENT DOCUMENTS

| 5,389,369 | A | 2/1995 | Allen et al. |
| 5,607,681 | A | 3/1997 | Galley et al. |
| 6,149,908 | A | 11/2000 | Claesson et al. |
| 6,156,792 | A | 12/2000 | Hatton et al. |
| 6,214,339 | B1 | 4/2001 | Pellico |
| 6,277,891 | B1* | 8/2001 | Sanders et al. ................ 514/742 |
| 6,528,081 | B1 | 3/2003 | Zellner |
| 2005/0238635 | A1* | 10/2005 | Tano ............................ 424/94.4 |
| 2006/0073212 | A1 | 4/2006 | Palmer et al. |
| 2007/0026085 | A1 | 2/2007 | Chandler |

FOREIGN PATENT DOCUMENTS

| EP | 307376 A | 3/1989 |
| EP | 0500387 A2 | 8/1992 |
| GB | 2285218 A | 7/1995 |
| JP | 2003-516314 A | 5/2003 |
| JP | 2004-509147 A | 3/2004 |
| WO | 9526137 A1 | 10/1995 |
| WO | 01/19322 A2 | 3/2001 |
| WO | 02/24217 A1 | 3/2002 |
| WO | 03/080109 A | 10/2003 |
| WO | 03080109 A1 | 10/2003 |
| WO | 2007/045251 A2 | 4/2007 |

OTHER PUBLICATIONS

Dröge, Wulf "Free Radicals in the Physiological Control of Cell Function" Physiol. Rev., Jan. 2002, 82(1), pp. 47-95.*
Cai, H; Davis M.E.; Drummond, G.R.; Harrison, D.G."Induction of Endothelial NO Synthase by Hydrogen Peroxide via a Ca+2/Calmodulin-Dependent Protein Kinase II/Janus Kinase 2-Dependent Pathway" Arterioscler Thromb Vasc Biol., 2001,21,pp. 1571-1576.*
Chang, Antje, "Class 1—Oxidoreductases IV EC 1.1.2-1.1.99" Springer Handbbok of Enzymes, 2nd ed., Nov. 23, 2004, vol. 19, pp. xv-xvi only.*
International Search Report, dated Jun. 16, 2009, from corresponding PCT application, 6 pages.
Krister Tano, "Bacterial Ecology of the Nasopharynx in Relation to Otitis Media", Umea: University Medical Dissertations, New Series, No. 755, pp. 3-4, 37-48 and 55-59, 2001.
Krister Tano et al, "Inhibition of OM Pathogens by Alpha-Hemolytic Streptococci from Healthy Children, Children with SOM and Children with rAOM", Int'l. Journal of Pediatric OtoRhinoLaryngology, 56 (2000) 185-190.
Kristian Roos et al "Alpha-Streptococci as Supplementary Treatment of Recurrent Streptococcal Tonsillitis: A Randomized Placebo-Controlled Study", Scan J Infect Dis, 25:31-35, 1993.
Kristian Roos et al "Effect of recolonisation with "interfering" α streptococci on recurrences of acute and secretory otitis media in children: randomised placebo controlled trial", BMJ, vol. 322, 2001, pp. 1-4.
Krister Tano et al, "A nasal spray with alpha-haemolytic streptococci as long term prophylaxis against recurrent otitis media", Int'l Journal of Pediatric OtoRhinoLaryngology, 62 (2002) 17-23.
Krister Tano et al, "Is Hydrogen Peroxide Responsible for the Inhibitory Activity of α-haemolytic Streptococci Sampled from the Nasopharynx?", Acta Otolaryngol, 2003; 123:724-729.
J. Carlsson et al, Hydrogen Peroxide Excretion by Oral Streptococci and Effect of Lactoperoxidase-Thiocyanate-Hydrogen Peroxide, Infection and Immunity, vol. 40, No. 1, Apr. 1983, pp. 70-80.
J. Tenovuo et al, "Relationship of the human salivary peroxidase system to oral health", Journal of Oral Pathology, 1984:13, 573-584.
Pruitt et al, "The Lactoperoxidase System", School of Dental and Oral Surgery, Ref. 49, S.12 pp. 1-239 (1985), Marcel Dekkar Inc., N.Y.
Yoshio Uehara et al, "H2O2 Produced by Viridans Group Streptococci May Contribute to Inhibition of Methicillin-Resistant *Staphylococcus auereus* Colonization of Oral Cavities in Newborns", Clinical Infectious Diseases, 2001:32 pp. 1408-1413.

(Continued)

Primary Examiner — Jon P Weber
Assistant Examiner — Aaron J Kosar
(74) Attorney, Agent, or Firm — Porter Wright Morris & Arthur LLP

(57) ABSTRACT

A method for treatment and/or prevention of common cold caused by rhinovirus, wherein a patient in need is treated with a medicament including a hydrogen peroxide producing enzyme.

18 Claims, No Drawings

(56) References Cited

OTHER PUBLICATIONS

Murat Ünal et al, "Ringer-Lactate solution versus isotonic saline solution on mucociliary function after nasal septal surgery," The Journal of Laryngology & Otology, 2001, vol. 115, pp. 796-797.

Boek, Wilbert M. M.D. et al, "Physiologic and Hypertonic Saline Solutions Impair Ciliary Activity in Vitro", Laryngoscope, vol. 109(3), Mar. 1999, pp. 396-399.

Cecilia Giulivi et al, "Hydrogen Peroxide Production by Red Blood Cells", Free Radical Biology & Medicine, vol. 16, pp. 123-129, 1994.

M.T. Silva, "Electron Microscopic Study on the Effect of the Oxidation of Ultrathin Sections of *Bacillus cereus* and *Bacilus megaterium*", J. Ultrastructure Research, 18, 345-353 (1967).

B. Rosan et al, "Morphological Changes in *Streptococcus sanguis* Associated With Growth in the Presence of Oxygen" Archs oral Biol. vol. 18, pp. 1441-1444, 1973.

Takuji Ohwada et al, "Susceptibility to Hydrogen Peroxide and Catalase Activity of Root Nodule Bacteria", Biosci. Biotechnol. Biochem., 63 (3), 457-462, 1999.

Hélène M. Jouve et al, "Properties of a catalase from a peroxide-resistant mutant of *Proteus mirabilis*", Can. J. Biochem. Cell Biol., vol. 61, 1983, pp. 1219-1226.

Edwin L. Thomas et al, "Antibacterial Activity of Hydrogen Peroxide and the Lactoperoxidase-Hydrogen Peroxide-Thiocyanate System against Oral Streptococci", Infection and Immunity, vol. 62, No. 2, Feb. 1994, pp. 529-535.

Adam J. Ratner et al, "Lactoperoxidase", Am. J. Respir. Cell Mol. Biol., vol. 22, No. 6, Jun. 2000, 642-644.

Saeki et al, Purification and Properties of NADH Oxidase from *Bacillu, megaterium*, 98 J. Biochem. 1433-1440 (1985).

Pitkäranta et al, "Rhinoviruses: Important Respiratory Pathogens." Annals of Medicine, 30(6):529-537 (1998).

Dowell et al, Otitis Media—Principals of Judicious Use of Antimicrobial Agents, 101 Pediatrics 165, 169 (1998).

Alper et al, "Rate of Concurrent Otitis Media in Upper Respiratory Tract Infections with Specific Viruses," Arch Otolaryngology Head Neck Surgery, 135:17-21 (2009).

Mentel et al, "Virus Inactivation by Hydrogen Peroxide," Vopr Virusol, 6:731-3 (1977) (abstract only).

Chonmaitree, Viral and Bacterial Interaction in Acute Otitis Media:, Pediatric Infectious Disease Journal, 19(5):S24-30 (2000).

Ruohola et al, "Microbiology of Acute Otitis Media in children with Tympanostomy Tubes: Prevalences of Bacteria and Viruses," Clinical Infectious Diseases, 43:1417-1422 (2006).

Chonmaitree et al, "Viral Upper Respiratory Tract Infection and Otitis Media Complication in Young Children," Clinical Infectious Diseases, 46:815-823 (2008).

Chonmaitree et al, "Acute Otitis Media is not a Pure Bacterial Disease," Clinical Infectious Diseases, 43:1423-1425 (2006).

Mentel et al, "Investigations on rhinovirus inactivation by hydrogen peroxide", Acta Virologica, 17(4):351-354 (1973).

Mentel et al, "Experiments in chemical inactivation of rhino- and coronal viruses", Zeitschrift fur die Gesamte Hygiene und Ihre Grenzgebiete, 20(8):530-533 (1974), including English summary.

Barbara Watt et al, "Hydrogen Peroxide Poisoning", Toxicological Review, 23(1):51-57 (2004).

Extended European Search Report form Corresponding EP 09721305.2 dated May 19, 2011.

Jul. 2, 2013 Official Action from corresponding Japanese Application No. 2011-500740, including English Summary, 5 pages.

Ohnishi et al, Bull. Chem. Soc. Jpn., 64:3581-3584 (1991).

\* cited by examiner

USE OF A SUBSTANCE FOR MANUFACTURING OF A MEDICAMENT FOR TREATMENT OF COMMON COLD

FIELD OF THE INVENTION

The present invention relates to treatment and/or prevention of a disease caused by rhinoviruses.

BACKGROUND TO THE INVENTION

It is well known that the normal bacterial flora in the upper respiratory airways is of significant importance in preventing overgrowth of pathogenic bacteria and subsequent infection. Most of the bacteria of the normal flora consist of alpha haemolytic streptococci (AHS). It has been shown that one of the most important mechanisms used by AHS in order to inhibit growth of the rhinosinusitis and otitis media pathogens, is to produce considerable amounts of hydrogen peroxide, $H_2O_2$ [1].

The hydrogen peroxide also contributes as a substrate for lactoperoxidase (LPO), a member of the non-specific defence system of the nasopharyngeal mucosa. Lactoperoxidase is dependent of hydrogen peroxide for production of hypothiocyanate, $OSCN^-$, a more potent antibacterial substance. The normal bacterial flora including AHS and the human mucosa have a natural protection against both hydrogen peroxide and hypothiocyanate [2].

While the use of a hydrogen producing enzyme in ointment around the skin and nasal orifices for treatment of staphylococci has been disclosed previously, this is a treatment directed towards the bacteria of the skin flora, a parallel to the hydrogen peroxide containing ointment Microcid™.

EP 1 490 096 disclose the use of a hydrogen peroxide producing nasal spray for treatment of otitis media, preferably in children. However, while there are several antibiotics intended to treat otitis media, there is no proved active treatment against the common cold caused by Rhinovirus.

SUMMARY OF THE INVENTION

In the present invention it has surprisingly been found that it is possible to use a hydrogen peroxide producing enzyme to inactivate Rhinovirus causing common cold.

One embodiment of the present invention is related to a method for treatment and/or prevention of a disease, caused by a Rhinovirus, wherein a patient in need is treated with a medicament comprising a hydrogen peroxide producing enzyme.

In a further embodiment of the present invention, the hydrogen peroxide producing enzyme is selected from the group consisting of: Glucose oxidase, xylitol oxidase, mannitol oxidase, lactate oxidase, galactose oxidase and glycerol oxidase.

In another embodiment of the present invention, the hydrogen peroxide producing enzyme is glucose oxidase combined with amyloglucosidase.

In one embodiment of the present invention, the disease is the common cold.

In a further embodiment of the present invention, the hydrogen peroxide producing enzyme is formulated in Ringer's solution.

In another embodiment of the present invention, the medicament is water soluble.

In one embodiment of the present invention, the medicament is formulated as a nasal spray.

In a further embodiment of the present invention, the medicament is formulated as nose drops.

In another embodiment of the present invention, an enzyme substrate is added to the medicament.

DETAILED DESCRIPTION OF THE INVENTION

Rhinoviruses (RV) are the most common agent causing common cold [3]. Furthermore, otitis media in children are often preceded by a common cold. RV is not a systemic infection, but is located in the nasal cavity and in the nasopharynx [4]. It is known that hydrogen peroxide can inactivate RV [5], but it is not possible to make a nasal spray comprising hydrogen peroxide in order to inactivate a RV infection due to several reasons:
a. Nasal distribution of a spray does not involve the posterior parts of the nasal cavity, where most of the viral particles are situated [6].
b. The enzyme catalase, which is abundant in the mucosal cells, would convert hydrogen peroxide into water and oxygen long before it would reach the posterior nasal area.
c. A sufficient hydrogen peroxide concentration would have to be high initially, and would therefore cause considerable irritation of the nasal mucosa [7].

There is so far no drug with a documented effect on an episode of common cold, other than symptomatic relief against for example a running nose.

In the present invention it has surprisingly been found that it is possible to use a hydrogen peroxide producing enzyme to permanently inactivate Rhinoviruses. It has been demonstrated that an incubation of only 30 minutes is sufficient to inactivate a considerable amount (>100 $TCID_{50}$) of a Rhinovirus inoculate in human tracheal cells. $TCID_{50}$ is defined to mean the concentration of virus needed, in order to visualize a cytopathic effect (=infection) in at least 50% of the inoculated vials. This means that it is possible to treat a common cold, where the Rhinovirus infection is situated in the posterior part of the nasal cavity. It could therefore not be foreseen that a hydrogen peroxide producing enzyme, such as GO, would have the following characteristics:
1. A permanent inactivation of rhinoviruses within 30 minutes.
2. A prevention of further infection of the cells, even if the addition of GO is made more than two days after the initial inoculation, which means that it is possible not only to prevent a common cold, but also to treat an infection after the onset of the symptoms.
3. A possibility to maintain a sufficient hydrogen peroxide concentration over time in nasopharynx, in order to inactivate all of the viral seats in the mucosa. Only then the symptoms of a common cold will disappear.

Surprisingly, all of the criteria above are met with a nasal spray containing GO and glucose, as shown in our experiments.

Glucose oxidase (GO) is a hydrogen peroxide producing enzyme, well tolerated for human use. Is is a natural ingredient in honey [8] and it has been used for many years as an antibacterial preservative. The hydrogen producing effect of GO has also been used as an antibacterial additive in different mouth rinses (Oral Balance™) and in toothpaste (Zendium™).

Amyloglucosidase (AGO) is an enzyme that produces glucose from starch and has its optimal effect at a temperature around 50-60° C. GO and AGO are sometimes combined in order to prevent the activation of GO at lower temperatures. When the solution meets the body temperature, AGO will start to release glucose and GO will produce hydrogen peroxide. Otherwise it would be necessary to use a two-chamber system in order to avoid the mixing of the enzyme (GO) and the substrate (glucose).

Suitable substrates for nasal use would for example be: xylitol (having an antibacterial effect in itself), mannitol (an adhesive effect against certain otitis media pathogens), lactate (innate substance), galactose, glycerol (good for the nasal mucosa) and glucose. This means that following hydrogen peroxide producing enzymes would fit as a medicament in a nasal spray against Rhinoviruses: Glucose oxidase, xylitol oxidase, mannitol oxidase, lactate oxidase, galactose oxidase and glycerol oxidase. Both galactose oxidase and glycerol oxidase are very lenient to human lung fibroblast cells (WI 38) according to our laboratory studies.

In another embodiment the hydrogen peroxide producing enzyme is glucose oxidase combined with amyloglucosidase.

Clinical studies have reported that Ringer's solution has a more beneficial effect on the mucociliary system of the nasal mucosa than physiological saline [9]. This could indicate that Ringer's solution is the preferable carrier solution for a pharmaceutical preparation in the nasal cavity.

The invention will now be described more closely in association with an experimental section.

The aim of the following description is to show that the inhibitory substance, hydrogen peroxide, produced by an enzyme, is able to inactivate Rhinoviruses causing common cold. Rhinoviruses (viruses belonging to the genus rhinovirus) is a causative agent for the common cold.

Previous studies have shown that AHS with good inhibitory activity could produce hydrogen peroxide at a level corresponding to a hydrogen peroxide concentration of about 10 mM (=0.03%). A glucose oxidase concentration, producing hydrogen peroxide concentrations of about 0.05% should thus be sufficient in order to mimic the effect in vivo of a normal bacterial flora with a very good inhibitory activity. The experiments below indicate that a GO concentration of less than 20 U/ml have an effect on the Rhinovirus infection, corresponding to a hydrogen peroxide concentration of more than 10 mM.

The experiments, described in example 1 and 2, revealed that a glucose oxidase concentration of 20 U/ml was sufficient to irreversibly inactivate the cytopathic effect of rhinovirus on the WI 38 cells. This inactivation was completed during an incubation time of less than 30 minutes, which would be sufficient in order to inactivate rhinovirus during the passing of glucose oxidase through the nose and nasopharynx, before it is swallowed down [10]. In the second example it was also possible to prevent further infection of the cells by rhinovirus, even if the glucose oxidase was added as late as 2 days after the initial incubation, which could suggest that a nasal spray with glucose oxidase could have a therapeutic effect on common cold, even after the onset of the symptoms.

The third example illustrates that a significant reduction of the signs of a common cold is achieved already after 12 hours of treatment. The inventor have used the nasal spray during the last three years during episodes of common cold and the pattern is nearly always the same: After frequent use of the nasal spray with GO, every second hour during the first 12 hours, and after that less frequent (2-4 times a day during the following 2-3 days), the symptoms of common cold disappears within 12-24 hours after beginning of the treatment. Also other volunteers have reported the same effects of the spray. These pilot studies show that the presence of GO is at a sufficient level long enough to inactivate the RV situated in the nose and nasopharynx.

Catalase quickly transforms hydrogen peroxide into oxygen and water, so it is not likely that it would function with a nasal spray containing hydrogen peroxide, especially as the rhinovirus often is situated on the adenoid in the nasopharynx [5]. Catalase is a specific enzyme catalyzing the conversion of $H_2O_2$ into $O_2$ and $H_2O$. This reaction proceeds rapidly. Purified catalase from human erythrocytes (>30 000 U/mg) was used in the experiments.

In the virus assays simulating common cold, two reference isolates from ATCC have been used, namely ATCC 1117 (=Rhinovirus 7) and ATCC 1118 (=Rhinovirus 8). The cell culture used in the experiments with the rhinoviruses is the recommended WI 38 cell line originating from human fetal lung fibroblasts and with an obvious cytopathic effect (CPE), when incubated together with a rhinovirus.

In the clinical studies with a nasal spray, comprising glucose oxidase, GO was used at a concentration of 100 U/ml in Ringer's solution together with a glucose spray, containing 5% beta-D glucose in isotonic solution. Each puff of the spray gives off 0.1 ml and in the experiments 2 puffs from each of the bottles (one bottle with GO, and one with glucose) were given as one dose.

Clinical pilot studies have suggested that a nasal spray containing 100 U Glucose Oxidase/ml together with a nasal spray containing 5% glucose solution is well tolerated and seem to shorten the duration of an episode of common cold.

The results of the nasal spray with GO are so far very promising and the inventor has received permission from the Ethical Committee and the Swedish Medical Products Agency to start a randomized, placebo-controlled and double-blinded study in order to investigate the possibilities of the nasal spray to shorten an episode of common cold.

EXAMPLES

Example 1

The objective of the following example is to show the effect of a hydrogen peroxide producing enzyme, glucose oxidase, on rhinoviruses, the cause of common cold.

Experiment 1

Virus: Rhinovirus 7, purchased from ATCC (VR-1117), was used as a representative for the rhinovirus group. In the assays the dilutions $10^{-2}$ and $10^{-3}$ were used. These concentrations should correlate to 100 $TCID_{50}$ and produced a clear and massive cytopathogenic effect (CPE) in previous dilution series, when assayed together with WI 38. 0.3 ml of each dilution was added into the vials.

Cell culture: Human lung cell fibroblasts (WI 38, ATCC-CCL-75) was used for cytopathic effect detection. 10-fold serial dilutions had been made from the concentrated viral suspension. 0.1 ml of a dilution of $10^{-4}$ to $10^{-5}$ was sufficient to produce visible cytopathic effect within 5 days in 2 ml wells. A dilution of $10^{-3}$ or more was enough to destroy the majority of the cells after 5 days of inoculation. The cells were first cultured in RPMI with 10% fetal calf serum until a smooth layer was seen at the bottom of the wells. Then the media was changed to RPMI with 2% of fetal calf serum, which was preserved during the assay. The cells were incubated in $CO_2$ enriched air at 37° C. During the experiments a cell culture of $17^{th}$-$18^{th}$ passage was used.

Catalase: From Sigma-Aldrich™. A solution of 100 000 U/ml was prepared from the original solution of $10^6$ U/ml. 0.01 ml was added to the vials, which resulted in 1000 U/ml in the vials.

$H_2O_2$: a 20% solution was diluted in Phosphate buffered saline (PBS) to a 0.5% and a 0.05% solution. 0.1 ml was added to the vials, which means 0.05% or 0.005% in the vials.

REHYDREX™ with 2.5% glucose: 0.6 ml was used in each vial as a substrate for Glucose Oxidase.

Glucose oxidase (GO): From Sigma-Aldrich™. A solution of 200 U/ml and 600 U/ml was prepared from the original solution of 6000 U/ml. 0.1 ml of each of the dilutions was added to the vials, which resulted in 20 U/ml or 60 U/ml of Glucose Oxidase in the vials.

In order to evaluate whether the effect of the hydrogen peroxide was a direct effect on the virus itself or a cytoprotective effect, we preincubated the virus with the hydrogen peroxide, before it was transferred to the wells with the cells. The WI 38 cells are also sensitive to hydrogen peroxide, and therefore it was necessary to add catalase before inoculation into the wells. Furthermore, inactivation of RV 7 by addition of catalase demonstrated the velocity of this inactivation. This design would also reveal if the inhibitory effect was only a virostatic one, or if it could damage the virions irreversibly.

In table 1 the content of each of the 10 vials (Eppendorf) is listed. The vials were incubated in a heater keeping a stable temperature of 37° C. 1000 U of catalase was added after 15, 30 and 60 min of incubation. 2×50 µl from each vial was transferred to duplicate cell wells (a 96-well plate). As controls in the cell wells, we used (in duplicate): Cells+RPMI, cells+catalase, cells+Glucose Oxidase, cells+0.05% $H_2O_2$, cells+REHYDREX™, catalase+RV7 The cells were examined daily for 5 days and eventually after 7 days of incubation.

Table 1. Content of the Vials

TABLE 1

Content of the vials

| No. | | | |
|---|---|---|---|
| 1 | 0.6 ml of REHYDREX ™ | 0.3 ml RV 7 (dil $10^{-2}$) | 0.1 ml GO (20 U/ml) |
| 2 | 0.6 ml of REHYDREX ™ | 0.3 ml RV 7 (dil $10^{-2}$) | 0.1 ml GO (60 U/ml) |
| 3 | 0.6 ml of REHYDREX ™ | 0.3 ml RV 7 (dil $10^{-2}$) | 0.1 ml 0.05% $H_2O_2$ |
| 4 | 0.6 ml of REHYDREX ™ | 0.3 ml RV 7 (dil $10^{-2}$) | 0.1 ml 0.5% $H_2O_2$ |
| 5 | 0.7 ml of REHYDREX ™ | 0.3 ml RV 7 (dil $10^{-2}$) | |
| 6 | 0.6 ml of REHYDREX ™ | 0.3 ml RV 7 (dil $10^{-3}$) | 0.1 ml GO (20 U/ml) |
| 7 | 0.6 ml of REHYDREX ™ | 0.3 ml RV 7 (dil $10^{-3}$) | 0.1 ml GO (60 U/ml) |
| 8 | 0.6 ml of REHYDREX ™ | 0.3 ml RV 7 (dil $10^{-3}$) | 0.1 ml 0.05% $H_2O_2$ |
| 9 | 0.6 ml of REHYDREX ™ | 0.3 ml RV 7 (dil $10^{-3}$) | 0.1 ml 0.5% $H_2O_2$ |
| 10 | 0.7 ml of REHYDREX ™ | 0.3 ml RV 7 (dil $10^{-3}$) | |

The WI 38 cells were sensitive to a severe toxic effect of 0.05% $H_2O_2$ and a slight toxic effect of the enzyme Glucose Oxidase (GO). However the slight toxic effect of Glucose Oxidase did not prevent the possibility to examine the cells regarding the cytopathic effect of RV 7.

After 5 days of incubation there was no cytopathic effect in the wells where the Glucose Oxidase had been incubated with RV 7. Not even in the wells after only 15 min of incubation and with the higher concentration of RV 7. A Glucose Oxidase concentration of 20 U/ml, seemed to be sufficient to achieve a complete inactivation of the RV 7. See Table 2.

TABLE 2

| Content | Day 3 | Day 5 | Day 7 | Preincubation time |
|---|---|---|---|---|
| 20 UGO/ml + RV (2dil) | − | − | − | 15 min |
| 0.005% $H_2O_2$ + RV (2dil) | + | ++ | ++ | " |
| 0.05% $H_2O_2$ + RV (2dil) | − | − | − | " |
| RV (2 dil, = $10^{-2}$) | + | ++ | ++ | " |
| 20 UGO/ml + RV (3dil) | − | − | − | " |
| 0.005% $H_2O_2$ + RV (3dil) | − | + | + | " |
| 0.05% $H_2O_2$ + RV (3dil) | − | − | − | " |
| RV (3 dil, = $10^{-3}$) | + | + | ++ | " |
| 20 UGO/ml + RV (2dil) | − | − | − | 30 min |
| 0.005% $H_2O_2$ + RV (2dil) | + | + | ++ | " |
| 0.05% $H_2O_2$ + RV (2dil) | − | − | − | " |
| RV (2 dil, = $10^{-2}$) | + | ++ | ++ | " |
| 20 UGO/ml + RV (3dil) | − | − | − | " |
| 0.005% $H_2O_2$ + RV (3dil) | − | − | − | " |
| 0.05% $H_2O_2$ + RV (3dil) | − | − | − | " |
| RV (3 dil, = $10^{-3}$) | + | ++ | ++ | " |
| 20 UGO/ml + RV (2dil) | − | − | − | 60 min |
| 0.005% $H_2O_2$ + RV (2dil) | + | + | + | " |
| 0.05% $H_2O_2$ + RV (2dil) | − | − | − | " |
| RV (2 dil, = $10^{-2}$) | + | ++ | ++ | " |
| 20 UGO/ml + RV (3dil) | − | − | − | " |
| 0.005% $H_2O_2$ + RV (3dil) | − | − | − | " |
| 0.05% $H_2O_2$ + RV (3dil) | − | − | − | " |
| RV (3 dil, = $10^{-3}$) | + | + | ++ | " |
| 0.05% $H_2O_2$ | TOX | TOX | TOX | |
| Catalase 1000U | − | − | − | |
| GO 40 U/ml | (tox) | (tox) | (tox) | |

− = No infection and no toxic effect
+ or ++ = Positive cytopathic effect, viral infection
(tox) = Slight toxic effect, but the cells were not damaged. Same effect when incubated with 60 U GO/ml.
TOX = Damaged cells due to toxic effect, impossible to evaluate Regarding the hydrogen peroxide, the lower concentration (0.005%, 2 mM) was not able to inactivate the higher concentration of RV 7. However, after 60 min of incubation the 0.005% hydrogen peroxide solution was able to inactivate the RV 7 at the $10^{-3}$ dilution. At the 0.05% (20 mM) solution the $H_2O_2$ was able to inactivate the RV 7 at all concentrations and already after 15 min of incubation. The amount of $H_2O_2$ produced by 20 U/ml of Glucose Oxidase would thus be equivalent to more than 0.005% $H_2O_2$. The results above were identical after 7 days of incubation.

During the 7 days of incubation there was no sign of recovery of the inactivated RV 7 in the wells, where the Glucose Oxidase or the 0.05% hydrogen peroxide solution had been assayed. This indicates that the inactivation of the RV 7 was irreversible, and not only virostatic.

Experiment 2

Experiment on Rhinovirus 7 and 8 with WI 38 cells and glucose oxidase (GO)
Glukosoxidase: 6000 U/ml=>0.07 ml to 2 ml PBS=200 U/ml
Catalase: One million U/ml=>0.01 ml to 1 ml PBS=10 kU/ml
Hydrogen peroxide: 10% solution=>0.02 ml to 2 ml PBS=0.1% solution
Cells: WI 38 in RPMI+2% fetal calf serum.
Rhinovirus: ATCC 1117(=Rv nr 7) and ATCC 1118(=Rv 8)
Virus dilution: 0.1 ml undiluted virus solution from ATCC to 0.7 ml PBS=Dilution 1 0.1 ml from dil 1 to 0.9 ml PBS=Dilution 2, etc to dilution 5.
Incubation:
0.7 ml 5% glucose solution+0.1 ml dil 1 of RV7 (=a7) or RV8 (=a8)+0.2 ml Glucose Oxidase solution according to above (final concentration in the vial 40 U/ml). Virus concentration=dil 2. Incubation during 30 min in heater keeping 37° C. After 30 min the effect of the hydrogen peroxide is aborted with the addition of 0.1 ml catalase solution into the vial (=1 kU/ml).

0.7 ml 5% glucose solution+0.1 ml dil 1 of RV7 (=a7) or RV8 (=a8)+0.1 ml of the hydrogen peroxide solution (=final concentration in the vial=0.01%). Incubation and abortion of the hydrogen peroxide effect similar as in a).

Altogether 4 vials (Eppendorff): a7, a8, b7 and b8.

After the addition of catalase, samples are transferred to a 96-well plate with flat bottom according to table 3. After 2 days of incubation in 37° C. with $CO_2$, 10 U of Glucose Oxidase is added into 8 of the wells+0.1 ml 5% of glucose solution. The wells with added Glucose Oxidase is depicted in the table 4. RV 8 was a more efficient pathogen than RV 7, but a concentration of 40 U/ml of Glucose Oxidase was able to inactivate both RV 7 and RV 8, in spite of the high initial inoculate. It seemed that addition of Glucose Oxidase into the wells 2 days after the initial incubation, could prevent the spread of viral infection to other cells than the cells already affected.

TABLE 3

Inoculation of WI 38 cells (071110) and RV 7 and RV 8.

| | | | | | | | |
|---|---|---|---|---|---|---|---|
| 50 μl R7s1 | R7sp1 | R7sp2 | R7sp2 | R7sp2 | R7sp3 | R7sp3 | R7sp3 |
| 50 μl R8s1 | R8sp1 | R8sp2 | R8sp2 | R8sp2 | R8sp3 | R8sp3 | R8sp3 |
| 50 μl R7s4 | R7sp4 | R7sp4 | R7sp4 | R7sp5 | R7sp5 | R7sp5 | R7sp5 |
| 50 μl R8s4 | R8sp4 | R8sp4 | R8sp4 | R8sp5 | R8sp5 | R8sp5 | R8sp5 |
| 10 μl R7s1 | 10 μl R7s1 | 10 μl R7s1 | | | 10 μl R7s2 | 10 μl R7s2 | 10 μl R7s2 |
| 10 μl R8s1 | 10 μl R8s1 | 10 μl R8s1 | | | 10 μl R8s2 | 10 μl R8s2 | 10 μl R8s2 |
| 50 μl a7 | 50 μl a7 | 50 μl a7 | 50 μl a7 | 50 μl b7 | 5 μl b7 | 50 μl b7 | 50 μl b7 |
| 50 μl a8 | 50 μl a8 | 50 μl a8 | 50 μl a8 | 50 μl b8 | 50 μl b8 | 50 μl b8 | 50 μl b8 |
| 10 μl R7s1 | 10 μl R7s1 | 10 μl R7s1 | 10 μl R7s1 | 10 μl R8s1 | 10 μl R8s1 | 10 μl R8s1 | 10 μl R8s1 |
| H2O2 + RV 7 | H2O2 + RV 7 | 0.003% H2O2 | 0.003% H2O2 | 0.003% H2O2 | 0.003% H2O2 | 0.003% H2O2 | 0.003% H2O2 |
| 50 UGO/ml | 50 UGO, PBS | Medium | 5% glc | 5% glc | PBS | 2 kU catalase | 2 kU/ml catalase |
| 50 U/ml GO | 50UGO, PBS | Medium | 5% glc | 5% glc | PBS | 2 kU/ml catalase | 2 kU/ml catalase |
| H | G | F | E | D | C | B | A |

TABLE 4

Experiment 071110, after 2 and 10 days, respectively.

After 2 days of inoculation
Experiment 071110, after 2 days*

| | | | | | | | |
|---|---|---|---|---|---|---|---|
| 1 | 3+ | 3+ | 1+ | 1+ | 1+ | 1+ | 1+ | 1+ |
| 2 | 3+ | 3+ | 2+ | 2+ | 2+ | 2+ | 2+ | 1+ |
| 3 | 1+ | 0 | 0 | 1+ | 0 | 0 | 0 | 0 |
| 4 | 1+ | 1+ | 1+ | 1+ | 0 | 0 | 0 | 0 |
| 5 | 3+ | 3+ | 3+ | 0 | 0 | 1+ | 1+ | 1+ |
| 6 | 3+ | 3+ | 3+ | 0 | 0 | 3+ | 3+ | 3+ |
| 7 | 0 | 0 | 0 | 0 | 1+ | 1+ | 1+ | 1+ |
| 8 | 0 | 0 | 0 | 0 | 1+ | 1+ | 1+ | 1+ |
| 9 | 2+ | 1+ | 1+ | 1+ | 2+ | 3+ | 3+ | 3+ |
| 10 | Tox | Tox | Tox | Tox | Tox | Tox | Tox | Tox |
| 11 | tox | tox | 0 | 0 | 0 | tox | 0 | 0 |
| 12 | tox | tox | 0 | 0 | 0 | tox | 0 | 0 |
| | H | G | F | E | D | C | B | A |

After 10 days of inoculation
Experiment 071110, after 10 days**

| | | | | | | | |
|---|---|---|---|---|---|---|---|
| 1 | 3+ | 3+ | 3+ | 2+ | 3+ | 2+ | 1+ | 1+ |
| 2 | 3+ | 3+ | 3+ | 2+ | 3+ | 3+ | 3+ | 3+ |
| 3 | 1+ | 0 | 0 | 0 | 0 | 0 | 0 | 0 |
| 4 | 3+ | 3+ | 3+ | 0 | 0 | 0 | 3+ | 0 |
| 5 | 3+ | 3+ | 3+ | 0 | 0 | 2+ | 2+ | 2+ |
| 6 | 3+ | 3+ | 3+ | 0 | 0 | 3+ | 3+ | 3+ |
| 7 | 0 | 0 | 0 | 0 | 1+ | 2+ | 2+ | 2+ |
| 8 | 0 | 0 | 0 | 0 | 3+ | 3+ | 3+ | 3+ |
| 9 | 3+ | 3+ | 1+ | 1+ | 2+ | 3+ | 3+ | 3+ |
| 10 | tox | tox | tox | tox | tox | tox | tox | tox |
| 11 | tox | tox | 0 | 0 | 0 | tox | 0 | 0 |
| 12 | tox | tox | 0 | 0 | 0 | tox | 0 | 0 |
| | H | G | F | E | D | C | B | A |

*10 U GO was added to cells E1, E2, E3, E4, F9, E9, D9, and C9 after 2 days of incubation
1+ = Only a few infected cells or groups of cells
2+ = Scattered infection - about half of the cells are affected, but still a lot of uninfected cells
3+ = Disseminated infection - scarcely any uninfected cells visible
Tox = toxic effect on the cells - the cells not possible to evaluate regarding CPE
**In general more difficult to evaluate the cells because of disintegration of the infected cells

Example 3

The objective of the following example is to evaluate the optimal concentration and dose of a nasal spray containing glucose oxidase in a pilote clinical trial to treat common cold.

Experiment 3

The test person, K.T., aimed to investigate if a nasal spray containing 100 U/ml Glucose Oxidase, together with a nasal spray containing 5% of glucose, could reverse the symptoms of a common cold.

The spray was not supposed to be used as a prophylactic, but only after symptoms as rhinitis together with blocked nose and/or sneezing. The symptoms were graded in a scale from 0-5 and at the end of the day the symptoms were re-evaluated with the same scale. For details regarding the protocol see Table 5.

It seemed as if the nasal spray was used as often as every 2 hours during the first day of treatment, it was sufficient to reverse the symptoms as rhinitis, blocked nose and sneezing within one day. It is probably necessary to continue the treatment at least 2-3 times daily for the next days in order to prevent the disease from coming back. No other side effects have been observed than a feeling of dryness in the nose, which disappears when the treatment is over.

TABLE 5

Protocol for tests of Glucose oxidase nasal spray
Name: K. T.

| Date | Time | Cause for spraying | | | Dose: # Puffs | Symptom after 30 min | | | Comments, and other medicaments |
|------|------|---------|------------|--------|-------|---------|------------|--------|------|
|      |      | Nasal catarrh | Nasal congestion | Sneeze |       | Nasal catarrh | Nasal congestion | Sneeze |      |
| 6/4  | 8    | 4 | 3 | 3 | 2 + 2 | 2 | 1 | 1 |  |
|      | 10   | 4 | 4 | 4 | 2 + 2 | 3 | 2 | 2 |  |
|      | 12   | 4 | 4 | 4 | 2 + 2 | 3 | 2 | 2 |  |
|      | 14   | 4 | 4 | 4 | 2 + 2 | 3 | 2 | 2 |  |
|      | 16   | 4 | 4 | 4 | 2 + 2 | 3 | 2 | 2 |  |
|      | 18   | 3 | 3 | 3 | 2 + 2 | 2 | 1 | 1 | Duration |
|      | 20   | 2 | 3 | 2 | 2 + 2 | 1 | 2 | 1 | 12 hours |
|      | 22   | 1 | 2 | 1 |       | 0 | 1 | 0 | of the cold |
| 14/4 | 18   | 3 |   | 3 | 2 + 2 | 0 |   | 0 |  |
| 17/11| 9    | 4 | 4 | 3 | 2 + 2 | 2 | 1 | 0 | Rinexin |
|      | 10   | 3 | 2 | 1 | 2 + 2 | 2 | 1 | 0 |  |
|      | 12   | 3 | 2 | 1 | 2 + 2 | 2 | 0 | 0 |  |
|      | 13   | 3 | 2 | 0 | 2 + 2 | 2 | 0 | 0 |  |
|      | 14   | 3 | 2 | 0 | 2 + 2 | 2 | 0 | 0 |  |
|      | 16   | 2 | 1 | 0 | 2 + 2 | 1 | 0 | 0 |  |
|      | 18   | 2 | 1 | 0 | 2 + 2 | 1 | 0 | 0 |  |
|      | 21   | 1 | 1 | 0 | 2 + 2 | 0 | 0 | 0 |  |
|      | 24   | 1 | 1 | 0 | 2 + 2 | 0 | 0 | 0 |  |
| 18/11| 6    | 3 | 2 | 0 | 2 + 2 | 1 | 0 | 0 | Rinexin |
|      | 12   | 2 | 1 | 0 | 2 + 2 | 0 | 0 | 0 |  |
|      | 18   | 2 | 0 | 0 | 2 + 2 | 0 | 0 | 0 |  |
| 19/11| 8    | 1 | 1 | 0 | 2 + 2 | 0 | 0 | 0 |  |
|      | 18   | 1 | 1 | 0 | 2 + 2 | 0 | 0 | 0 |  |
| 20/11| 8    | 1 | 0 | 0 | 2 + 2 | 0 | 0 | 0 | Well |
|      | 20   | 1 | 0 | 0 | 1 + 1 | 0 | 0 | 0 |  |

Time = Time of the day
Symptoms were graded from "0" (=no problem) to "5" (=significant inconvenience)
Comments, and other medicaments: Side effects, other medicaments taken, endurance of the cold etc
Dose: Normal dose is 2 puffs of Glucose oxidase and 2 puffs of glucose (="2 + 2")
The interval between doses: 1-2 hours at the beginning of the disease
The patient should avoid sniffing in so much that the liquid enters the lungs

REFERENCES

[1] Tano K, Grahn Håkansson E, Wallbrandt P, Rönnqvist D, Holm S E, Hellström S. Is hydrogen peroxide responsible for the inhibitory activity of alpha-haemolytic streptococci sampled from nasopharynx? Acta Otolaryngol 2003; 123: 724-729.

[2] Carlsson J, Iwami Y, Yamada T; Hydrogen Peroxide Excretion by Oral Streptococci and Effect of Lactoperoxidase-Thiocyanate Hydrogen Peroxide. Infect Immun 1983; 40: 70-80.

[3] Papadopoulos N G, Johnston S L. Rhinoviruses. Principles and Practice of Clinical Virology, 5$^{th}$ ed. 2004. Wiley&Sons Ltd. pp 361-373.

[4] Winther B, Gwaltney J M, Mygind N, Turner R B, Hendley J O. Sites of Rhinovirus Recovery after Point Inoculation of the Upper Airway. JAMA 1986; 13:1763-1767.

[5] Mentel R, Schmidt J. Investigations on Rhinovirus Inactivation by Hydrogen Peroxide. Acta Virol 1973; 17:351-354.

[6] Bateman N D, Whymark A D, Clifton N J, Woolford T J. A study of intranasal distribution of Asselstine hydrochloride aqueous nasal spray with different spray techniques. Clin Otolaryngol. 2002; 27:327-330.

[7] Greiff L, Ejerfält I, Ejerfält JS, Wollmer P, Persson CGA. Effects of hydrogen peroxide on the guinea-pig tracheobronchial mucosa in vivo. Acta Physiol Scand 1999; 165: 415-420.

[8] Bang L M, Buntting C, Molan P. The effect of Dilution on the Raye of Hydrogen Peroxide Production in Honey and its Implications for Wound Healing. J of Alternative and Complementary Medicine 2003; 9:267-273.

[9] Unal M, Gorur K, Ozcan C; Ringer-Lactate solution versus Isotonic Saline solution on Mucociliary function after nasal septal surgery. J Laryngol Otol 2001; 115:796-7.

[10] Newman S P, Morén F, Clarke S W. Deposition pattern from a nasal pump spray. Rhinology 1987; 25:77-82.

The invention claimed is:

1. A method for treatment of a disease, caused by a Rhinovirus, comprising administering to a patient having said disease a medicament comprising a hydrogen peroxide producing enzyme.

2. The method according to claim 1, wherein the hydrogen peroxide producing enzyme is selected from the group consisting of: glucose oxidase, xylitol oxidase, mannitol oxidase, lactate oxidase, galactose oxidase and glycerol oxidase.

3. The method according to claim 1, wherein the hydrogen peroxide producing enzyme is glucose oxidase and is administered with amyloglucosidase.

4. The method according to claim 1, wherein the disease is the common cold.

5. The method according to claim 4, wherein the medicament is formulated as a nasal spray and administered nasally.

6. The method according to claim 1, wherein the hydrogen peroxide producing enzyme is formulated in Ringer's solution.

7. The method according to claim 1, wherein the medicament is water soluble.

8. The method according to claim 1, wherein the medicament is formulated as a nasal spray and administered nasally.

9. The method according to claim 1, wherein the medicament is formulated as nose drops and administered nasally.

10. The method according to claim 1, wherein an enzyme substrate is added to the medicament.

11. The method according to claim 9, wherein the hydrogen peroxide producing enzyme is glucose oxidase and the medicament comprises from 20 U/ml to 100 U/ml glucose oxidase.

12. The method according to claim 11, wherein the hydrogen peroxide producing enzyme is glucose oxidase and the medicament comprises 100 U/ml glucose oxidase.

13. The method according to claim 11, wherein glucose oxidase is co-administered with a separate nasal spray containing glucose.

14. The method according to claim 13, wherein the nasal spray contains 5% glucose.

15. The method according to claim 1, wherein the medicament is administered every two hours in the first 12 hours of treatment.

16. The method according to claim 15, wherein the medicament is administered 2 to 4 times a day after the first 12 hours of treatment.

17. A method for treatment of a disease caused by a Rhinovirus, wherein the disease is the common cold, comprising nasally administering to a patient having said disease a medicament comprising glucose oxidase.

18. The method according to claim 17, wherein the medicament comprises from 20 U/ml to 100 U/ml glucose oxidase and is co-administered with a separate nasal spray containing glucose.

* * * * *